(12) United States Patent
Eriksson et al.

(10) Patent No.: US 11,127,279 B2
(45) Date of Patent: Sep. 21, 2021

(54) USAGE DETECTION OF HYGIENE EQUIPMENT

(71) Applicant: Essity Hygiene and Health Aktiebolag, Gothenburg (SE)

(72) Inventors: John Eriksson, Gothenburg (SE); Annie Thorburn, Ellos (SE); Hakan Lindstrom, Gothenburg (SE)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 0 days.

(21) Appl. No.: 16/765,652

(22) PCT Filed: Nov. 29, 2018

(86) PCT No.: PCT/EP2018/082981
§ 371 (c)(1),
(2) Date: May 20, 2020

(87) PCT Pub. No.: WO2019/106078
PCT Pub. Date: Jun. 6, 2019

(65) Prior Publication Data
US 2020/0302774 A1   Sep. 24, 2020

(30) Foreign Application Priority Data

Nov. 29, 2017   (WO) ................. PCT/EP2017/080797

(51) Int. Cl.
*G08B 23/00* (2006.01)
*G08B 21/24* (2006.01)
(Continued)

(52) U.S. Cl.
CPC ........... *G08B 21/245* (2013.01); *G16H 40/20* (2018.01); *H04W 4/38* (2018.02)

(58) Field of Classification Search
CPC .......... G08B 21/245; A47K 2010/3226; A47K 5/1217
See application file for complete search history.

(56) References Cited

U.S. PATENT DOCUMENTS 8,237,558 B2 * 8/2012 Seyed Momen ..... G01S 1/7034
340/539.11
8,587,437 B2   11/2013 Kyle et al.
(Continued)

FOREIGN PATENT DOCUMENTS

CN    104603805 A    5/2015
CN    105164737 A   12/2015
(Continued)

OTHER PUBLICATIONS

European Patent Office, International Search Report and Written Opinion of the International Searching Authority, International Application No. PCT/EP2017/080797, dated Aug. 8, 2018 (13 pages).

(Continued)

*Primary Examiner* — Toan N Pham
(74) *Attorney, Agent, or Firm* — Wood Herron & Evans LLP

(57) ABSTRACT

A detection and reporting device for determining a usage event indicating a use of a piece of hygiene equipment, the detection and reporting device comprising a positioning section that allows determining positional information indicating a position of the detection and reporting device; a sensor section configured to sense over a time span an observable indicating a use of the piece of hygiene equipment and to generate usage event information on the basis of the sensed observable; and a reporting section configured to generate and transmit a message on the basis of said usage (Continued)

event information and on information allowing an association to said positional information.

19 Claims, 5 Drawing Sheets

(51) Int. Cl.
 *G16H 40/20* (2018.01)
 *H04W 4/38* (2018.01)

(56) References Cited

U.S. PATENT DOCUMENTS

| | | | |
|---|---|---|---|
| 9,027,795 B2* | 5/2015 | Zaima | B05B 11/308 222/175 |
| 9,619,989 B1 | 4/2017 | Ewing et al. | |
| 9,836,950 B2* | 12/2017 | Levchenko | G07C 9/28 |
| 10,004,364 B2 | 6/2018 | Hyland | |
| 10,373,477 B1* | 8/2019 | Bonner | A47K 5/12 |
| 10,607,471 B2* | 3/2020 | Hood | G16H 40/20 |
| 2008/0103636 A1 | 5/2008 | Glenn et al. | |
| 2010/0173581 A1 | 7/2010 | Dolan | |
| 2012/0218106 A1* | 8/2012 | Zaima | B05B 12/02 340/540 |
| 2013/0033376 A1 | 2/2013 | Seyed Momen et al. | |
| 2013/0216370 A1 | 8/2013 | Roth et al. | |
| 2015/0227705 A1 | 8/2015 | Zaima et al. | |
| 2016/0140831 A1 | 5/2016 | Hermann et al. | |
| 2017/0098366 A1 | 4/2017 | Hood et al. | |

FOREIGN PATENT DOCUMENTS

| | | |
|---|---|---|
| IE | 20070081 A1 | 10/2007 |
| RU | 2510282 C2 | 3/2014 |
| WO | 2010141689 A2 | 12/2010 |
| WO | 2015087331 A1 | 6/2015 |
| WO | 2015144845 A1 | 10/2015 |

OTHER PUBLICATIONS

European Patent Office, International Search Report and Written Opinion of the International Searching Authority, International Application No. PCT/EP2018/082981, dated Feb. 22, 2019 (15 pages).
New Zealand Intellectual Property Office, Patent examination report 1, Application No. 763793, dated Aug. 25, 2020 (7 pages).
The Federal Service for Intellectual Property, Office Action, Russian Application No. 2020119547/03, dated Oct. 23, 2020 (11 pages).
IP Australia, Examination report No. 1 for standard patent application, Application No. 2018376322, dated Dec. 15, 2020 (4 pages).
National Intellectual Property Administration (CNIPA) of the People's Republic of China, Notification of the First Office Action, Application No. 201880076545.7, dated May 21, 2021 (21 pages).

* cited by examiner

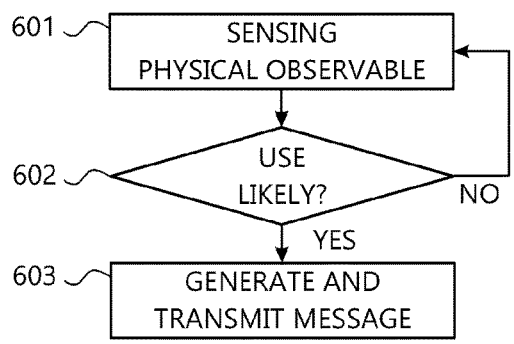
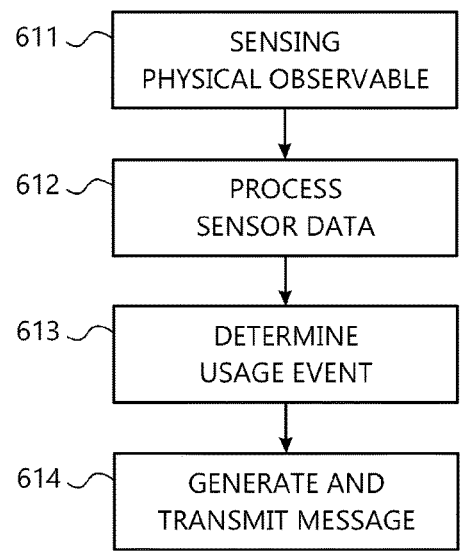
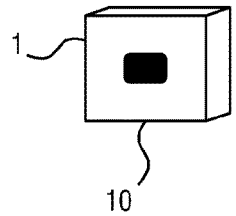
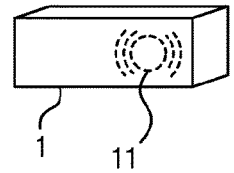
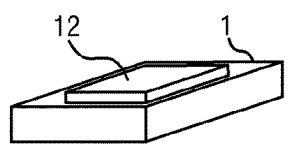
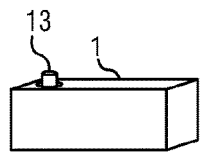
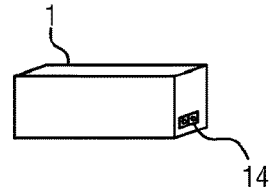
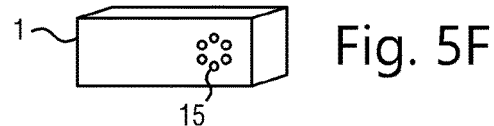
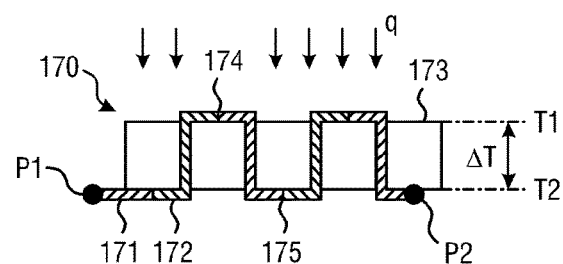
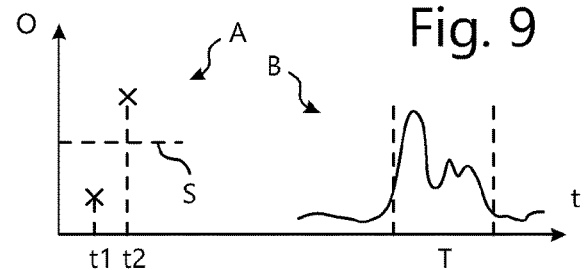

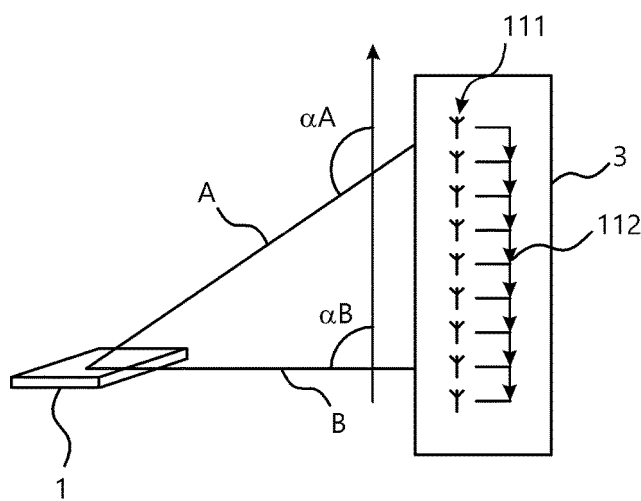
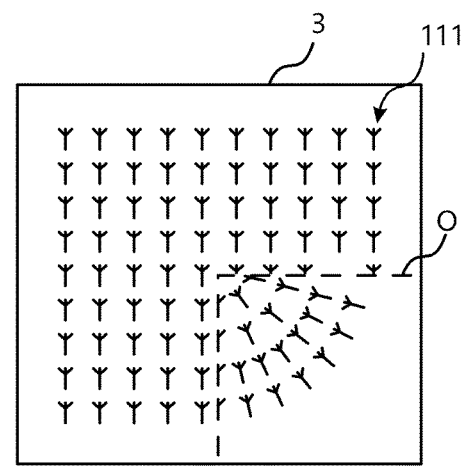
Fig. 7A
Fig. 7B
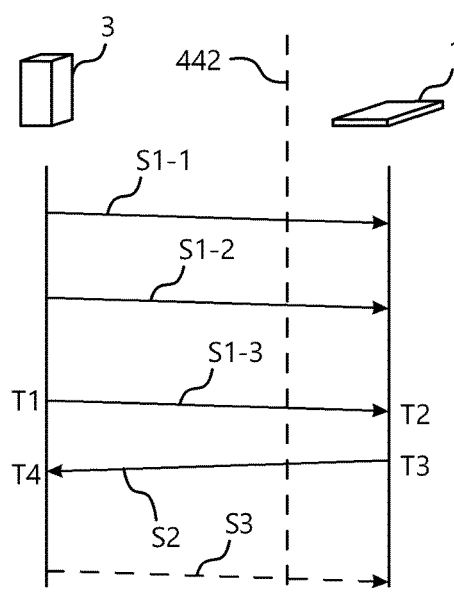
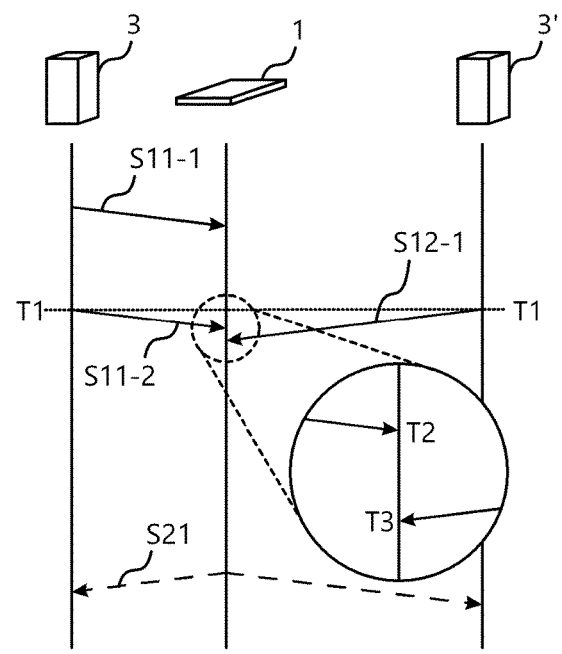
Fig. 8A
Fig. 8B

USAGE DETECTION OF HYGIENE EQUIPMENT

CROSS-REFERENCE TO RELATED APPLICATION

The present application is a national stage entry under 35 U.S.C. § 371 of, and claims priority to, International Application No. PCT/EP2018/082981, filed Nov. 29, 2018, which claims priority to International Application No. PCT/EP2017/080797, filed Nov. 29, 2017, the disclosures of which are hereby incorporated herein by reference in their entireties.

FIELD OF THE INVENTION

The present invention generally relates to determining usage event of hygiene equipment, such as soap, disinfectant, and/or towel dispensers, glove dispensers, and the like. More particularly, the present invention relates to a device that can accompany a piece of hygiene equipment and that detects a usage event thereof, i.e., which helps in determining whether or not a specific piece of hygiene equipment has been used.

BACKGROUND OF THE INVENTION

Hygiene equipment is commonplace today in many facilities, such as hospitals, medical service centers, intensive care units, day clinics, private practices, lavatories, rest rooms, hotels, restaurants, cafes, food service places, schools, kindergartens, manufacturing sites, administration and office buildings, and, in general, places and facilities that are accessible to the public or to a considerable number of individuals. The mentioned hygiene equipment thereby includes various types of individual devices and installations such as soap dispensers, dispensers for disinfectant solutions, gels or substances, towel dispensers, glove dispensers, tissue dispensers, carton boxes containing consumables such as gloves, tissues, etc., hand dryers, sinks, radiation assisted disinfectant points, ultraviolet (UV) light, and the like.

Although such hygiene equipment is commonplace today in many places, the use thereof by the individuals visiting these places or working in these places is still oftentimes not satisfactory. For example, hospitals, and, in general, medical service centers often suffer from hygiene deficiencies, which, in turn, may lead to the spread of infections and related diseases. In particular, such insufficient hygiene amongst medical care personnel coming into close contact with patients and bodily fluids can lead to the spread of infectious diseases amongst the personnel and other patients. It is also known that infections by highly resistant bacteria pose a severe problem in such places, especially in hospitals. In general, so-called Healthcare Associated Infections (HAI) are a real and tangible global problem in today's healthcare. HAI can be found to be currently the primary cause of death for 140.000 patients/year, affecting millions more and costs society in the range of billions of EUR/year.

At the same time, however, it is known that hygiene, and, in particular, hand hygiene, is an important factor as far as the spread of infectious diseases are concerned. Specifically, medical care personnel should make proper use of hand hygiene as often as possible so that the spread of bacteria and other disease causing substances is minimized. The actual usage of such hygiene equipment, however, may depend on—amongst others—the management of the facility, accessibility and usability of the equipment, culture, the cooperation and will exercised by the individuals working in these places or visiting such places, training of individuals, time pressure and possibly also other factors. In other words, an important factor remains the fact that individuals may not make use of installed and provided hygiene equipment although they are supposed to. Furthermore, it is generally accepted that an increased use of hygiene equipment can substantially contribute in reducing the spread of bacteria and the like, which, in turn, can drastically reduce the appearance of related infections and diseases. A further factor here may be an appropriate use of hygiene equipment, i.e., a determination whether a piece of hygiene equipment has been used at the right time and, possibly also, place. In other words, just using hygiene equipment to a large extent may yield an increased use of consumables but may not contribute as such in an improved compliance.

For example, a corresponding relatively "low" compliance may indicate that the actual use of hygiene equipment is not satisfactory, whilst relatively "high" compliance may indicate that the actual use of hygiene equipment corresponds, within a given threshold, to some target usage, and, consequently, may be regarded as being satisfactory. A tangible figure for estimating the quality of hygiene compliance may be found in a so-called compliance metric that as such may provide many advantages, since it can give a concise picture to operators of the corresponding facility so that they may initiate measures for increasing and promoting the actual use of hygiene equipment.

There are already ways of estimating such compliance in the arts, wherein the conventional approaches usually rely on measuring and/or observing "manually" by a human observer so-called opportunities and comparing these obtained opportunities to a measured/detected actual use of the hygiene equipment. In other words, the opportunities indicate any event when hygiene equipment should or could have been used. By then comparing this "should/could"-value to an actual usage value a compliance metric can be calculated. In general, the opportunities can be well defined figures, since they may be associated to specific rules and/or recommendations. For example, the World Health Organization (WHO) has defined the so-called "Five Moments Of Hand Hygiene" (cf. www.who.int/psc/tools/Five_moments/en/) including as explicit definitions for opportunities: 1. Before patient contact; 2. Before aseptic task; 3. After body fluid exposure risk; 4. After patient contact; and 5. After contact with patient surroundings. Moreover, measurements on corresponding hand hygiene compliance are becoming a regulatory requirement for the healthcare sector and may serve as an important quality improvement tool.

One of the main factors for determining a compliance metric, or, in general, some figure that indicates the usage of hygiene equipment, is the determination of usage events, i.e., the detection of the events whenever a piece of hygiene equipment has been used. Since the hygiene equipment is usually distributed over some kind of premises (e.g., a hospital building), the detection of usage events involves observing a large number of pieces of hygiene equipment. This, in turn, requires the individual pieces (e.g., a dispenser) to be able to detect usage events and report them to some kind of central entity (e.g., server) for data collection and analysis. Further, it is usually desirable to associate a specific piece of hygiene equipment to each detected event, so that information can be obtained on which pieces of hygiene equipment are used where and when. While obtaining timing information can be implemented more simply by timestamping any received events, the former determination of where a used piece of hygiene equipment is located can involve more complicated configurations and installations.

For the latter, it is already known to manually configure individual pieces of hygiene equipment with some kind of unique identifier or location information so that any received event information can be associated to a specific, for example, dispenser. This then usually allows respective data analysis, in the sense that a hospital management can determine that some wards use the provided hygiene equipment in a compliant manner, whereas the use of hygiene equipment may need to be promoted in some other ward. Such manual configuration may be, however, burdensome especially during installation and setting up of the system. Moreover, the individual pieces of hygiene equipment need to provide all the involved abilities, including, for example, the ability to detect a usage event, configurability, and the ability to correspondingly report any usage event with any associated identifier configured. At the same time, however, there already exists a large number of pieces of hygiene equipment in the mentioned premises, so that the prior arts usually require to replace any existing hygiene equipment by hygiene equipment that provides the required functionalities. Further, hygiene equipment may also be mobile as, for example, dispensers mounted on trolleys, equipment, etc., or there are even dispensers that can be carried by the users themselves in the form of, e.g., pocket-sized dispensers. In such instances it may not be of primary importance to determine what piece of hygiene has been used, but rather where and when it was used.

There is therefore a need for an improved concept for providing the ability to detect and report usage events in the context of hygiene equipment. It is further preferable to employ any existing installations of hygiene equipment to the largest extent possible and render both installation and operation as simple and reliable as possible.

SUMMARY OF THE INVENTION

The mentioned problems and drawbacks are addressed by the subject matter of the present invention.

According to an embodiment of the present invention, there is provided a detection and reporting device for determining a usage event indicating a use of a piece of hygiene equipment, the detection and reporting device comprising a positioning section that allows determining positional information indicating a position of the detection and reporting device; a sensor section configured to sense over a time span an observable indicating a use of the piece of hygiene equipment and to generate usage event information on the basis of the sensed observable; and a reporting section configured to generate and transmit a message on the basis of said usage event information and on information allowing an association to said positional information.

According to another embodiment of the present invention, there is provided a detection and reporting device comprising a positioning section that allows determining positional information indicating a position of the detection and reporting device; a sensor section configured to sense over a time span an observable indicating a use of the piece of hygiene equipment and to generate usage event information on the basis of the sensed observable; and a reporting section configured to generate and transmit a message on the basis of said usage event information and on information allowing an association to said positional information.

According to another embodiment of the present invention, there is provided a method for detecting a usage event indicating a use of a piece of hygiene equipment, comprising the steps of: determining positional information indicating a position of the detection and reporting device; sensing over a time span an observable indicating a use of the piece of hygiene equipment and generating usage event information on the basis of the sensed observable; and generating and transmitting a message on the basis of said usage event information and on information allowing an association to said positional information.

BRIEF DESCRIPTION OF THE DRAWINGS

Embodiments of the present invention, which are presented for better understanding the inventive concepts but which are not to be seen as limiting the invention, will now be described with reference to the figures in which:

FIGS. 5A to 5F show schematic views of detection and reporting devices according to respective embodiments of the present invention;

FIG. 5G shows a schematic view of a sensor element according to an embodiment of the present invention;

FIGS. 6A and 6B show flow charts of general method embodiments of the present invention;

FIGS. 7A and 7B show schematic views of locating and positioning schemes applicable for at least some embodiments of the present invention;

FIGS. 8A and 8B show schematic views of ranging and positioning schemes applicable for at least some embodiments of the present invention; and FIG. 9 shows a schematic and exemplary graph for values of an observable over a time span according to another embodiment of the present invention.

DETAILED DESCRIPTION OF THE INVENTION

Figure 1:
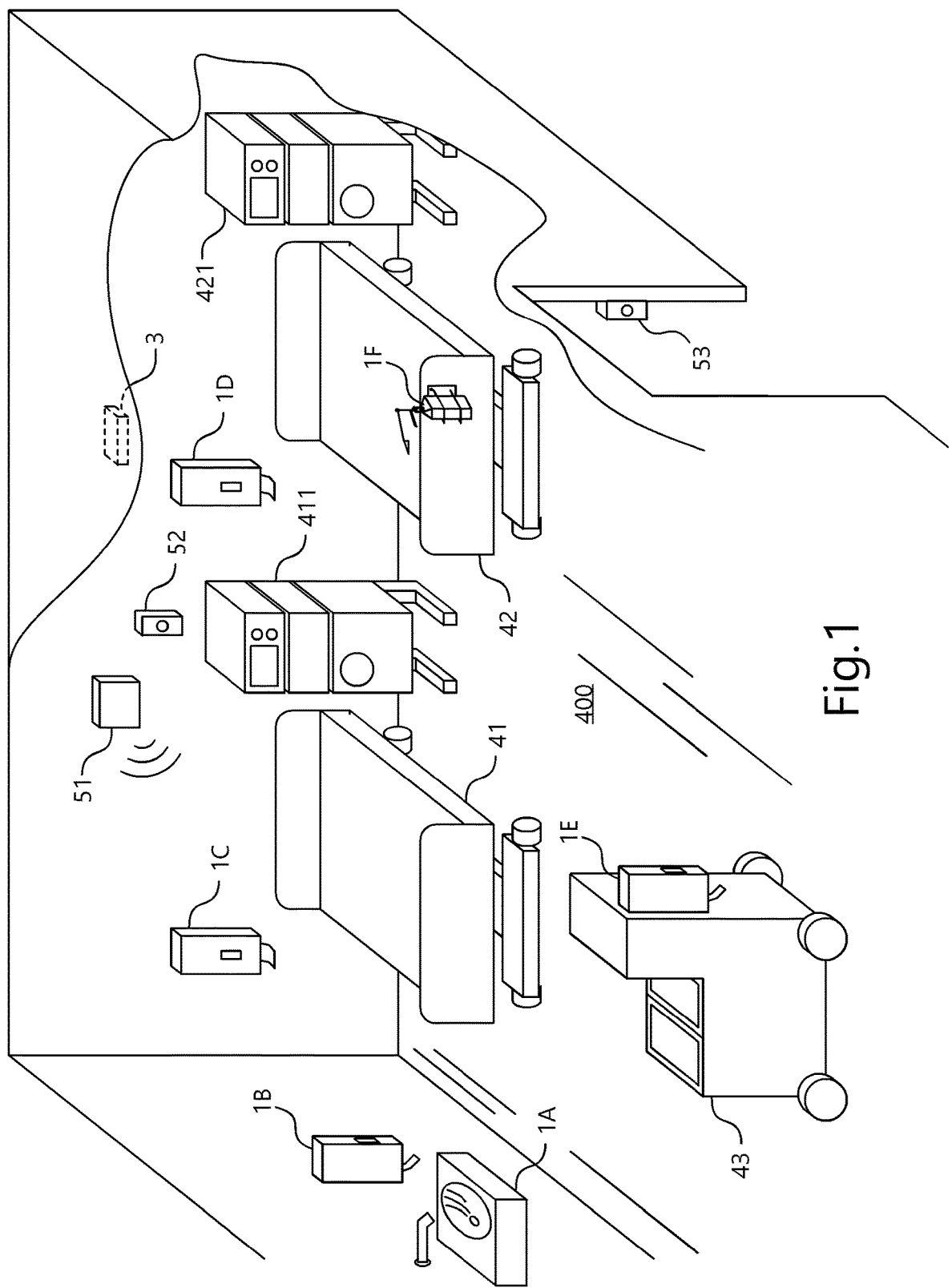
FIG. 1 shows a schematic view of a typical environment where the actual usage of hygiene equipment is subject to compliance.

FIG. 1 shows a schematic view of a typical environment where the actual usage of hygiene equipment is subject to compliance, and where the individuals are usually encouraged to use the hygiene equipment at specific instances. As an example, there is shown as a facility an intensive care unit 400 with corresponding intensive care points: first and second patient stations 41, 42 and first and second patient care equipment 411, 421. As can be seen, the intensive care unit 400 may be occupied by one or two patients in the shown configuration, whilst the embodiments of the present invention may envisage also other intensive care units with any number of patients and personnel and/or other facilities as mentioned elsewhere in the present disclosure. Examples for other possible working environments include hospitals and medical service centers in general, day clinics, private practices, lavatories, rest rooms, hotels, restaurants, cafes, food service places, schools, kindergartens, manufacturing sites, administration and office buildings, and, in broad terms, places and facilities that are accessible to the public or to a considerable number of individuals.

The configuration shown in FIG. 1 can acquire data indicating the usage of the hygiene equipment from equipment sensor arrangement provided for or in one or more of the individual pieces of hygiene equipment, such as a washing sink 1A, a soap dispenser 1B, and a first and a second disinfectant dispenser 1C, 1D, and a mobile piece of hygiene equipment 1E on a service trolley 43 and 1F mounted on bed 42. As regards the latter mobile pieces of hygiene equipment, it should be noted that the determined position for this may be of great interest and advantage. Since the dispenser is mobile, the position together with a use can indicate whether the piece of hygiene equipment has been used at the right place, and, possibly, at the right time. The position can also be put into relation with other objects, such as patients, beds, stations, zones, equipment, and the like. The position can be generally acquired and determined by the mechanisms as explained in greater detail below, or other suitable mechanisms, such as positioning by light signals and positioning by sound or ultrasonic signals.

Further examples for mobile equipment, such as bed 42 or trolley 43, include computers or instruments on wheels (ultrasonic imaging systems, respirators, etc.), medicine trolleys, instrument trolleys, or pieces of hygiene equipment that can be carried by the users themselves, such as pocket size disinfectant dispensers. Therefore, an embodiment of the present invention provides a detection and reporting device that is configured to accompany a mobile piece of hygiene equipment, such as dispensers 1E and 1F. This can be, for example, achieved in that the device is attached to the respective piece of hygiene equipment (e.g., dispenser).

The system should further be able to receive usage data from these pieces of equipment 1A-1F as possibly individual reports from each corresponding device/sensor. Likewise, opportunities to use the hygiene equipment can be detected by corresponding sensors including a vicinity sensor 51, a light barrier sensor 52 and a door passing sensor 53. The data on the usage and on the opportunities can be collected and processed for calculating a hygiene compliance metric or indicator, which, in turn, indicated to what degree the individuals (e.g., nurses, doctors, and caretakers) use the hygiene equipment at appropriate opportunities. Normally, the data generated by the distributed equipment 1A, 1B, 1C, 1D, 1E, 1F, 51, 52, and 53 is retrieved by some kind of central data processing and storage entity (not shown, e.g., a server), where the hygiene compliance metric is calculated.

In addition to the above, a positioning device 3 may be provided and that may be mounted, for example, on a ceiling of the room as shown. This positioning device 3 may assist in positioning tags, devices, and/or detection and reporting devices as also subject to the present disclosure. The main purpose of a positioning device 3 can be to locate another device inside room 400 in order to attribute data or detection results to a specific location, and, with this, to a specific piece of hygiene equipment. The functionalities and features of a suitable positioning device 3 are described in conjunction with FIGS. 7A, 7B, 8A, and 8B.

In general, it is noted that the positioning may serve several purposes: Firstly, by automated positioning of devices in conjunction with usually fixed pieces of hygiene equipment (e.g., dispenser 1B) would dispense with a need to "manually" configure the system with regard to information that indicates what dispenser is located at what position or in what ward. Secondly, pieces of hygiene equipment may as such be "mobile", as in the case of, for example, the dispenser 1E mounted on a trolley. Here, information on a position may have further benefits. Specifically, it can be determined what user used the hygiene equipment at what place and—optionally—at what time. So, in general, the detection and reporting device can further comprise a time keeping section that provides time information, and the reporting section can then be configured to generate said message further on the basis of said time information. Additionally or alternatively, the time information can also be determined and generated when any signals are received from a piece of hygiene equipment assuming that the time of sending is not substantially delayed. All this information can contribute in obtaining a figure or metric on compliance which ultimately attempts to define how the hygienic equipment is used, i.e., whether the users use hygiene equipment at the appropriate opportunities.

Figure 2:
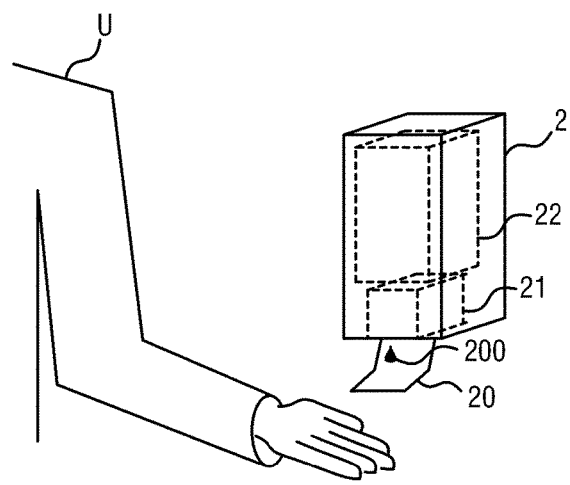
FIG. 2 shows a schematic view of a scenario of a usage event in the context of hygiene equipment.

FIG. 2 shows a schematic view of a scenario of a usage event in the context of hygiene equipment. As an example piece of hygiene equipment, a soap or disinfectant dispenser 2 is shown. This dispenser 2 can be used by a user U, who usually operates some kind of operating member 20 so as to cause the dispenser 2 to eject some amount 200 of consumable (soap, alcogel, etc.). For this purpose, the dispenser 2 usually comprises an ejection mechanism 21 and a reservoir 22 of the consumable. For example, the mechanical force exerted by user U to the lever 20 when operating the dispenser 2 actuates a pump within ejection mechanism 21. The pump ejects an amount 200 of the consumable from the reservoir 22 to, for example, the user's U palm.

In general, ejection mechanisms as shown in FIG. 2 may generate some kind of vibration or sound during operation. This lies in the very nature of dispensers as examples for pieces of hygiene equipment since some kind of mass needs to be ejected from a reservoir toward a user. In such cases, liquids are usually pumped, which, in turn, involves the actuation of a piston, a compressible enclosure, and/or a valve. Likewise, the dispensing of dry items such as tissues and towels generates some kind of vibration and/or noise. In general, however, hygiene equipment can also be virtually vibration-less or sound-less. A reason for that may lie in the mechanism involved which may generate only little vibration/sound, which, in turn, may be difficult to detect or distinguish from background sounds and vibrations that are usually present in all real life environments. However, the piece of hygiene equipment may be as such vibration- and sound-less, when, for example, radiation assisted hygiene measures are employed. For example, ultraviolet (UV) assisted hygiene equipment may be completely noiseless since the generation of UV light may not produce noise at all, but still a substantial hygienic effect may be achieved. In such cases, the device 1 may be configured to sense a light intensity, preferably regarding an ultraviolet spectrum component, as the observable over time.

Figure 3A:
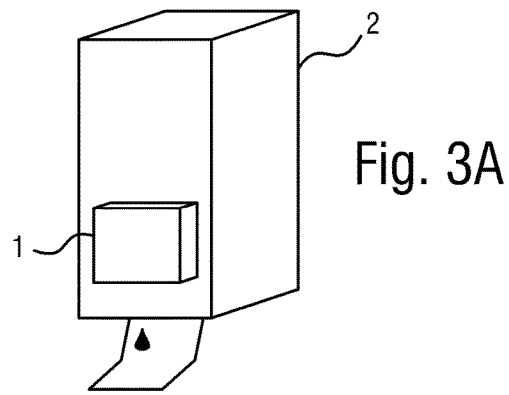
FIGS. 3A to 3L show schematic views of a deployment of a detection and reporting device according to respective embodiments of the present invention.
Figure 3B:
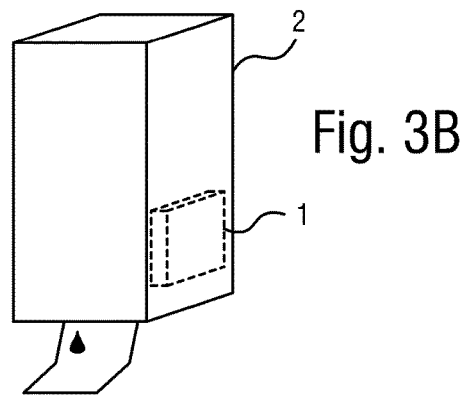
Figure 3C:
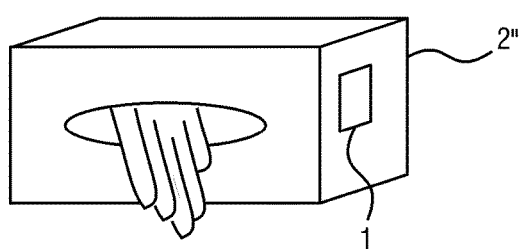

FIGS. 3A to 3C show schematic views of a deployment of a detection and reporting device according to respective embodiments of the present invention. In FIG. 3A, a detection and reporting device 1 (in the following "device 1") is attachable on a front side of a dispenser 2. In this way, the device 1 is configured to be attachable on a front surface of a dispenser device, which involves suitable fixing means (e.g., an adhesive tape/pad, a magnet, and/or bore(s) to receive a screw or rivet) and a suitable sensor section sensing over a time span a suitable observable that indicates a use of the piece of hygiene equipment 2. In the present embodiment, it may be preferable to employ any one of a proximity sensor on a front and/or lower side of the device 1, a vibration sensor, a sound sensor, and a thermal sensor (thermopile). However, further details for the employed sensor section are given elsewhere in the present disclosure.

In FIG. 3B, a device 1 is configured to be placed inside a housing of a dispenser 2. In this way, the device 1 can be primarily compatible with any residual spaces left inside the dispenser 2. This may involve a particular outer shape of the device 1 so as to fit into any suitable space available. Furthermore, the device 1 can be configured to be attachable on a respective inner surface of a dispenser device, which may involve suitable fixing means (e.g., an adhesive tape/pad, a magnet, and/or bore(s) to receive a screw or rivet). In this embodiment, a preferable sensor section may employ any one of a proximity sensor (e.g., capacitive so as not to be dependent on IR-light or other radiation penetrating the housing of dispenser 2), an EMC detector for sensing signals/interference or an electromagnetic field emitted from a motor other electric actuation mechanism during operation, a vibration sensor, and a sound sensor. In this embodiment, also a direct sensing may apply by means of, for example, a mechanical or electric coupling to the ejection mechanism. For example, a switch may be positioned so as to be operated by a mechanical member of the ejection mechanism whenever the dispenser is used. Also, an electric ejection mechanism may be envisaged which opens the transmission of an electric signal.

In FIG. 3C, a device 1 is configured to be attached to a box like dispenser 2", including, for example, carton and/or plastic boxes for dispensing consumables, such as gloves, tissues, etc. Here, it may be preferable for the device 1 to be attachable to an outside of the box dispenser 2" by means of an adhesive and/or removable fixing tape/pad. The device 1 can also be configured in a disposable fashion so that it is used only for one (carton) box of, e.g., gloves and is disposed of whenever the box run empty of consumables. As for these embodiments, a device 1 may preferably be configured to sense a vibration and/or a sound from the box like dispenser.

Figure 3D:
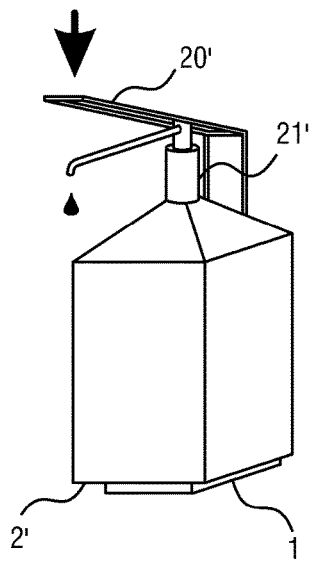

In FIG. 3D, a device 1 is configured to be placed under a dispenser 2. This embodiment may be preferable for dispensers 2' that are operated by means of applying a force with at least a vertical component. As shown, the dispenser 2' is provided with a pump mechanism 21' that is, in turn, actuated with a lever 20' that can be pushed downwards. As a consequence, a downward force may be applied to the entire dispenser 2' whenever used and operated. This opens specifically the possibility to place the detection and reporting device 1 (device 1) underneath the dispenser 2' and to provide the former with a pressure or weight sensor as part of the respective sensor section. More details are given in conjunction with FIG. 5C.

Figure 3E:
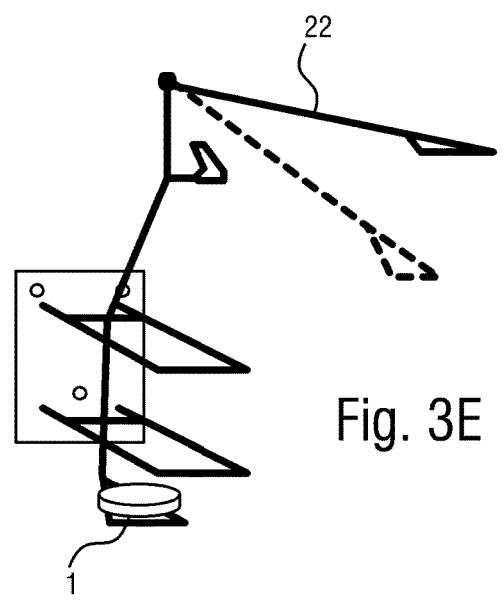

In FIG. 3E, a wire-frame like bracket 22 is shown as a part of a dispenser. Usually, such frames are configured to hold a pump-bottle or other type of container for a consumable hygiene product (e.g., soap, alcohol, etc.). In such embodiments, the container of the consumable is simply inserted into the wire-frame and is operated by means of a lever that engages with a pump-mechanism of the bottle in a fashion similar to that shown in conjunction with FIG. 3D. In this embodiment, the device 1 can be configured disk-like so as to fit in a lower part of the wire-frame. Specifically, the device 1 may be provided with a fitting groove that is configured to engage with a wire of a wire-frame dispenser holder. Such dispenser or holders may be preferably mounted also onto beds so that they can also move. Also, during cleaning and/or refilling the dispensers may move and "re-appear" at a somewhat unknown position at a later point and time so that it can be advantageous to obtain the information indicating a position of the device 1.

Figure 3F:
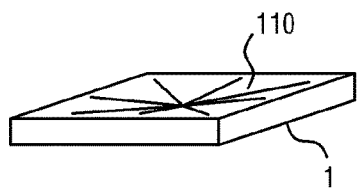

FIG. 3F shows a schematic view of a deployment of a detection and reporting device according to another embodiment of the present invention. Specifically, the device 1 takes here a form of a drip plate with a sink or pit 110. This recess 110 can be used to receive and collect remainders of any agent when placed underneath a piece of hygiene equipment. For the example of an disinfectant agent dispenser, the drip plate/tray can be placed underneath a nozzle opening of that dispenser so as to receive any drops or amounts of agent that may be spilled when a user applies ejects and applies that agent to his/her hands. A further advantage may lay here in that disinfectant agents may anyway require a drip plate to be placed underneath a dispenser, since the agent may otherwise damage surfaces or elements of the nearer vicinity (e.g., surface of floor, desk, furniture, or equipment finishing). In this way, the functionalities of a detection and reporting device can be advantageously combined with that of a drip plate.

It is to be noted, however, that a sink, pit or other recessed portion is not important or essential for any drip plate/tray embodiments of the present invention. Therefore, also flat drip trays may be envisaged that merely catch any remainders so that they do not come into contact with any materials under the drip tray. Any collected substances may evaporate and/or removed by, for example, a cleaning/maintenance procedure. In some embodiments, the sensor section of the detection and reporting device in the form of a drip plate or tray may comprise a thermopile sensor that points upwards, i.e., toward a piece of hygiene equipment when placed underneath that. In this way, the sensor section may detect a varying heat radiated from a user's hand when and during operating the piece of hygiene equipment.

Figure 3G:
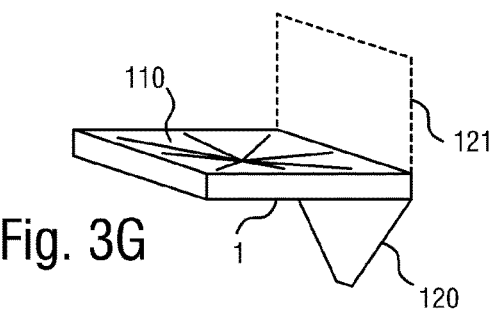

FIGS. 3G, 3H, 3I, and 3J show schematic views of further deployments of a detection and reporting device in the form of or comprising a drip plate according to respective embodiments of the present invention. In FIG. 3G, the device and drip plate 1 has a lower fixing plate 120 that can be in turn provided with means (e.g., holes, hooks, adhesive pad/tape, etc.) so that the device and plate 1 can be affixed to a wall or other surface underneath a piece of hygiene equipment. Optionally, the drip plate 1 may comprise a protecting section 121 that may be configured to protect a wall and/or other surroundings from spilled consumable.

Figure 3H:
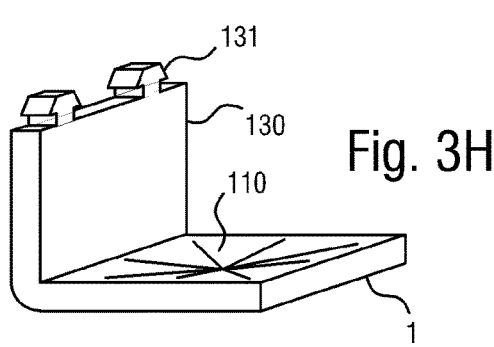

In FIG. 3H, there is shown an embodiment in which the detection and reporting device 1 in the form of or comprising a drip plate can be mounted to the piece of hygiene equipment 2 by, for example, members 131 that engage with respective openings of the piece of hygiene equipment. In this way, the detection and reporting device 1 as shown in FIG. 3H can be easily clicked or snipped into a piece of hygiene equipment, e.g., a dispenser. It is to be noted that the thickness and/or height of an upper fixing plate 130 may be adapted to the piece of hygiene equipment, and it may be well again provided means including, e.g., holes, hooks, adhesive pad/tape, etc., so as to mount the device, and optionally also the piece of hygiene equipment as such, to a wall or surface.

Furthermore, the upper fixing plate 130 may be provided with adhesive pads or tapes so as to mount the piece of hygiene equipment to the device and drip plate 1, and that device and plate 1 together with the piece of hygiene equipment to a wall or surface. Further, the upper fixing plate 130 may be provided with holes that match in size and/or position holes of the piece of hygiene equipment so that both the device and the piece of hygiene equipment can be mounted together, for example, by means of screws. Such means may then replace the engagement members 131 so that they need not to be provided in related embodiments.

Figure 3I:
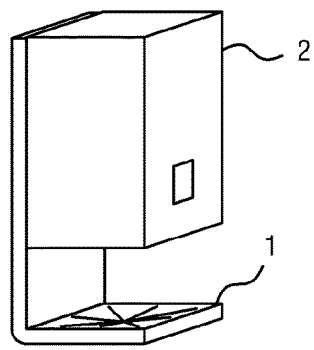

In FIG. 3I, there is shown an embodiment in which the detection and reporting device 1 in the form of or comprising a drip plate can be mounted together with the piece of hygiene equipment 2. Especially, this configuration refers to another embodiment of the present invention that provides a detection and reporting device that is configured to accompany a mobile piece of hygiene equipment. Specifically, the drip tray arrangement 1 as shown in FIG. 3I allows for a secure and reliable attaching to the respective piece of hygiene equipment (e.g., dispenser 2). As a consequence, the dispenser 2 may be mobile and mounted on, for example, some trolley and move around. Here, the positioning section of the detection and reporting device 1 can be of substantial advantage, since not only the position of the device but also the position of the dispenser and even the trolley can be obtained for any one of tracing, security, compliance determination and/or other purposes. However, this embodiment may also be employed when the detection and reporting device is wall-mounted together with the piece of hygiene equipment in a stationary configuration.

Figure 3J:
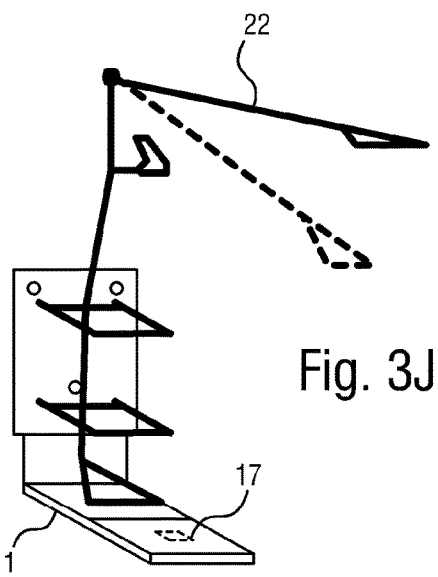

FIG. 3J shows a schematic view of a deployment of a drip tray embodiment in combination with a wire-frame like bracket 22 configured to hold a pump-bottle or other type of container for a consumable hygiene product (e.g., soap, alcohol, etc., cf. also FIG. 3E). Specifically, the detection and reporting device 1 shown in FIG. 3J can be mounted to or together with the frame 22 holding a pump-operated container and forming the piece of hygiene equipment. The area of the drip tray may at least extend to an area underneath a pump nozzle opening where it can be expected that spilled or ejected consumable (e.g., disinfectant agent) reaches to. In a related embodiment, the detection and reporting device is provided with a sensor section 17 employing a thermopile sensor pointing upwards, i.e., in a direction where the heat of a user's hand can be detected when or during using the piece of hygiene equipment.

Figure 3K:
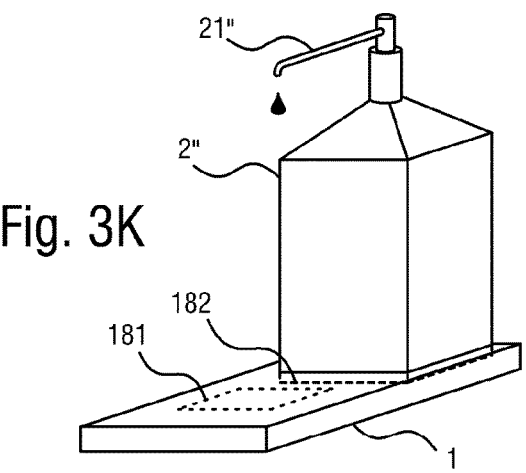

FIG. 3K shows a schematic view of a deployment of another drip tray embodiment in combination with a pump-bottle type piece 2" of hygiene equipment. Such pump-bottle like dispensers may provide a reservoir for a consumable hygiene product (e.g., soap, alcohol, etc., cf.) and a pump mechanism 21" for ejecting an amount if that consumable onto, for example, a user's hand. The drip tray 1 in this embodiment comprises an area 181 substantially underneath an ejection opening or nozzle of the pump mechanism 21".

The respective sensor element of the drip tray 1 as an embodiment of a detection and reporting device may be arranged in this area 181, e.g., in the form of a thermopile sensor element (see, also, description in conjunction with FIG. 5G). In this way, the detection and reporting device can detect an observable that indicates the use of the pump bottle 2" as a piece of hygiene equipment. The drip tray 1 may also comprise a fixation part 182, e.g., as a fitted recess, so as to receive and/or hold the piece 2" of hygiene equipment. In this way, a position of the sensor element inside or near area 181 relative to the piece of hygiene equipment 2", and—with this—an ejection opening for releasing a consumable, may be advantageously well defined.

Figure 3L:
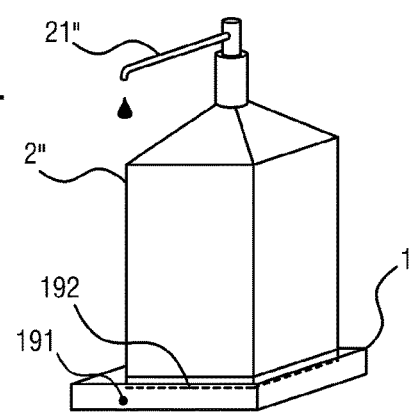

FIG. 3L shows a schematic view of a deployment of another drip tray embodiment in combination with a pump-bottle type piece 2" of hygiene equipment. This embodiment is similar to the drip tray as shown and described in connection with FIG. 3K, especially in relation to a fixation part, here denoted with 192, e.g., as a fitted recess, so as to receive and/or hold the piece 2" of hygiene equipment. However, the size of drip tray 1 as shown in FIG. 3L can be reduced by dispensing with a sensor area by employing another type of sensor 191, such as, for example, a buried pressure or force sensor element as described in conjunction with any one of FIGS. 5C and 5D. In particular, a buried force sensor 191 can be provided so as to detect a force/weight/pressure on an underside of the drip tray 1 which, when sensed as an observable, can indicate a pressure/force exerted onto the pump mechanism 2" and, with this, an instance of using the piece of hygiene equipment 2".

In general, whenever the detection and reporting device is orientated such that it has a field of view toward the (disinfectant) agent that is dispensed by a piece of hygiene equipment, the sensor can advantageously also consider the observable with regard to a time-of-flight which may allow also the detection of an actual ejection and/or an amount of ejected agent. Further details on such time-of-flight embodiments are given elsewhere in the present disclosure.

Figure 4:
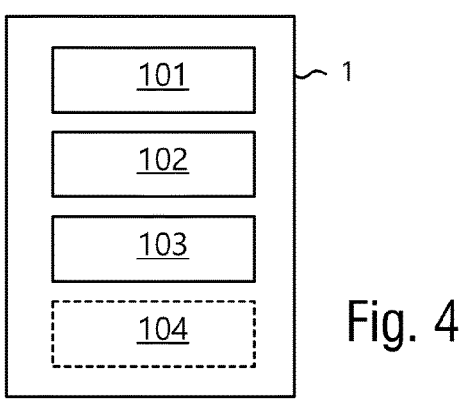
FIG. 4 shows a schematic view of a general apparatus embodiment for a detection and reporting device of the present invention.

FIG. 4 shows a schematic view of a general apparatus embodiment for a detection and reporting device of the present invention. Generally, a detection and reporting device 1 is used for determining a usage event indicating a use of a piece of hygiene equipment. The detection and reporting device 1 comprises a positioning section 101 that allows determining positional information indicating a position of the detection and reporting device. In some embodiments, the positioning section 101 is arranged to emit and/or receive one or more electromagnetic signals that can interplay with one or more positioning device(s). Such equipment being external to the detection and reporting device 1 is explained in greater detail in conjunction with FIGS. 7A to 8B. In any way, however, the positioning section 101 allows for determining information on a position of the detection and reporting device 1 so that such information can be reported together with any information relating to a usage of a piece of hygiene equipment. In some embodiments, the positional information is only obtained at specific times (including only once) and during the following operation usage events are associated with information on an identification of the detection and reporting device 1, wherein the information on the identification has been associated with a previously determined position.

The detection and reporting device 1 further comprises a sensor section 102 configured to sense over a time span an observable indicating a use of the piece of hygiene equipment and to generate usage event information on the basis of the sensed observable. The applicable types of observables and related measuring and sensing schemes are explained in greater detail in conjunction with FIGS. 5A through 5E. The detection and reporting device 1 comprises further a reporting section 103 that is configured to generate and transmit a message on the basis of said usage event information and on information allowing an association to said positional information. In this way, the detection and reporting device 1 can report the usage of specific pieces of hygiene equipment so that a remote entity (e.g., server) can obtain and analyze data on what piece of hygiene equipment was used.

In further embodiments of the present invention, the detection and reporting device 1 comprises an optional processing section 104 that is configured to process said usage event information for determining said usage event. Specifically, the locally obtained data on the observable can also be locally processed and analyzed with regard to determining a usage event as such and also with regard to additional information, the latter including information on an amount of ejected consumable and/or a type of consumable. In such cases, the reporting section 103 can be configured to generate and transmit a message when a usage event is determined, and the mere fact that a message is generated and transmitted may indicate the usage event. Any additional information and/or information on a position and/or identification of the device 1 can be conveyed with such a message to a central entity (e.g., server) for further data storage, processing and analysis.

FIGS. 5A to 5E show schematic views of detection and reporting devices according to respective embodiments of the present invention. In FIG. 5A, an embodiment is shown in which the detection and reporting device 1 (device 1) is provided with a sensor section that is configured to detect a proximity of an object as an observable over a time span. For this purpose, a window 10 may be provided for emitting and receiving an optical signal, such as an IR-light signal. The sensor section may comprise in this case an IR-light source which emits IR-light into the vicinity of the device 1, and, with this, of the piece of hygiene equipment to which the device 1 is attached.

At a first point in time, no object may be directly in front of the device 1 so that a first relatively low level of received IR-light intensity is detected as the observable. At a second point in time, for example, a user's hand, arm, or body may cause IR-light to be reflected so that a second relatively high level of received IR-light intensity is detected as the observable. In this way, two values of the observable in a time span may indicate a usage event of the respective piece of hygiene equipment. As an alternative to IR-light, visible or ultraviolet (UV) light may be employed. Furthermore, also a capacitive proximity sensing may be employed. As a further alternative, a thermopile may be employed which can comprise a passive sensor without emitting any detection light. Such a sensor may be configured to detect a temperature and a change thereof over time so that, for example, an approaching hand operating a piece of hygiene equipment can be detected.

Furthermore, a sensor may be configured to detect a movement of an object, e.g., by means of observing light, IR radiation, heat, ultrasound and the like. The corresponding observable can be observed over a time span and processed so as to determine the motion of an object, such as a body part or, more specifically, a hand. The obtained information may further be processed so as to determine a motion pattern. For example, the obtained movement information can be compared to prestored patterns that then allow an association to a specific action, such as an action of operating the piece of hygiene equipment. For example, pump mechanisms provided for ejecting a disinfectant will usually require some sort of specific actuation which can be mapped to corresponding target pattern to which a determined pattern can be compared.

Furthermore, a sensor may be configured to detect a time-of-flight measurement by means of, for example, detecting suitable light, radiation or sound signals that allow a determination of a time that the signal has taken from emission to again be detected. For example, a signal can be emitted at a known time and can be recaptured after having been reflected by an object. The determined time span of such an observable can make it possible to determine distance, location, and/or speed information. In a way, it can thus be provided for a means to allow to detect an actual ejection and/or an amount of actually ejected (disinfectant) agent. It may be helpful in such cases to place the sensor so that it faces an opening of the associated piece of hygiene equipment. For example, the sensor may be placed underneath a dispenser and aimed at the nozzle through which an agent is ejected.

Furthermore, a sensor may be configured to detect a concentration of a gas component in air, a concentration of a vapor component in air, and/or a concentration of a particle component in air. In this way, also the fact that some substance has been actually ejected can be reliably detected. As a preferred embodiment, the piece of hygiene equipment can be a dispenser that ejects an amount of disinfectant agent upon actuation. The agent can contain e.g., some kind of alcohol that can be "smelled" by such an olfactory sensor. The information of sudden presence of such substances in the environment of the device may thus not only be taken as indicating a use of a piece of hygiene equipment but also as an indication of actual ejection of an agent and, in turn, an indication of still available supply of that agent.

In FIG. 5B, an embodiment is shown in which the device 1 is provided with a sensor section that is configured to detect a vibration as an observable over a time span. For this purpose, a vibration sensor or accelerometer 11 may be provided for sensing a mechanical movement. Specifically, any operation of a mechanical ejection mechanism may involve some kind of vibration or other beat-like motion. This embodiment provides the sensing of such movement over a time span so as to measure a motion profile over time. In this way, the vibration/motion can not only be detected but also compared to specific predetermined vibration/motion pattern that can be associated with an actual usage event. Specifically, the detection can be tailored to a particular type of hygiene equipment which provides one or more vibration patterns whenever used. Such patterns can be attributed to the specific ejection mechanism employed and therefore may provide a possibility to distinguish vibration originating from an actual use of the associated piece of hygiene equipment from other vibrations that may be present in real-life environments (e.g., closing a door, moving a bed or equipment, moving a mobile trolley to which a piece of hygiene equipment is attached, moving of a user carrying a dispenser, and the like). According to another embodiment, a similar detection is based on sound, where a sound is sensed over a time span with a microphone. A sensed sound pattern can likewise be configured to one or more sound patterns that can be associated to a usage event.

In FIG. 5C, an embodiment is shown in which the device 1 is provided with a sensor section that is configured to detect a force or a weight. For this purpose, a force cell 12 may be provided for sensing a mechanical force exerted onto it. Specifically, a piece of hygiene equipment that is operated by means of exerting, for example, a manual force onto it could be observed by such a device 1. In this way, the device 1 can be placed underneath or behind a piece of hygiene equipment. If then a user pushes the piece of hygiene equipment down- or sideward for ejecting a consumable, the device 1 can detect the corresponding force. While it is possible to sense a force continuously and compare the measured result with some threshold value that indicates no use for determining whether or not a force rises during a usage event, it is also possible to record a force-over-time profile for determining additional information. Such additional information may relate to an amount of consumable ejected. For example, it is possible to sense how far a pump was activated by means of analyzing the sensed force over time or a force extremum during a usage event. Also, a mechanical hand pump (cf., for example, dispenser 2' of FIG. 3C) may take longer to relax and accordingly eject more consumable (e.g., disinfectant) if the pump has been pushed with a larger force.

In FIG. 5D, an embodiment is shown in which the device 1 is provided with a sensor section that is configured to detect a mechanical actuation. For this purpose, a mechanical switch 13 is provided which closes and/or opens an electric connection whenever operated. For example, such a device 1 can be placed inside a piece of hygiene equipment where the switch can be actuated by parts of a mechanical and/or electric expulsion mechanism. An observable would in this way be a digital signal that represents an open or closed switch. By comparing two measured signals at two different points in time, usage event can be determined. In a modified embodiment, the sensor section is configured to detect a force, such as an FSR force sensor. Such a sensor may enable an improved sensing ability, where one can easily adapt the force required for the trigger, i.e., the threshold for detecting an instance of a user using the piece of hygiene equipment. Such adaptation can be furthermore made dynamic, where, for example, a sensor output is set as a base level on the basis of a level that is kept for a predetermined time span. An interaction (i.e., instance of a user using the piece of hygiene equipment) is a given threshold above this base level. Such embodiments may prevent detection errors that are related to the weight of a piece of hygiene equipment in a case when, for example, the weight of the dispenser diminishes while agent is consumed (e.g., a full bottle or reservoir versus an empty bottle or reservoir).

In FIG. 5E, an embodiment is shown in which the device 1 is provided with a sensor section that is configured to detect an electric signal. For this purpose, a connector 14 is provided which allows an electrical connection to some other part of the piece of hygiene equipment. For example, such a device 1 can be placed inside a piece of hygiene equipment where a part of an electric expulsion mechanism can be directly connected. An observable would in this way be the signal being applied to connector 14. By comparing two measured signals at two different points in time, usage event can be determined. The signal applied to connector 14 may be, for example, a lower voltage level for indicating no current use of the piece of hygiene equipment, and can become a higher voltage level whenever active during a use. In additional embodiments, the connector 14 may also receive higher level digital signals from an expulsion mechanism for receiving additional information, such as a type or an amount of an ejected consumable (e.g., disinfectant).

In FIG. 5F, an embodiment is shown in which the device 1 is provided with a sensor section that is configured to detect any one of a concentration of a gas component in air, a concentration of a vapor component in air, and a concentration of a particle component in air. For this purpose, an opening 15 is provided which allows penetration of such substance to a sensor that can sense such presence or variations of such presence. These embodiments may employ the technology and concepts as they are known from gas or smoke detectors which can well detect the presence also of substances such as alcohol or other hygienic or disinfectant agents. By comparing two measured signals at two different points in time, usage event can be determined.

It is to be noted that such embodiments may not only be able to detect a use of a piece of hygiene equipment but also the actual ejection of an agent. This can add the information that agent was indeed ejected and can also be taken as information that there can be assumed sufficient supply of agent in the piece of hygiene equipment. Likewise, this information can be combined with sensing of any other observable as explained in conjunction with the present disclosure so as to determine a state in which a piece of hygiene equipment has run out of agent. For example, a first observable may be taken to determine a usage and the olfactory component/observable can be observed thereafter. If, for example, after a given time no confirmation of an ejection can be found by the olfactory observable, then the message can be provided with information that the piece of hygiene equipment may require a refill of agent.

FIG. 5G shows a schematic view of a sensor element according to an embodiment of the present invention. Specifically, a sensor element in the form of a thermopile sensor 170 is shown, that may form part of a sensor section as explained elsewhere in the present disclosure. An incident heat flux q may originate from the environment of the sensor element, and, with this, of a respective detection and reporting device. The heat flux q may specifically originate from a part of a human body such as a hand or an arm. The flux may be incident to the sensor element 170 via any one of an opening, an aperture, an optical system, a lens, and the like, which are elements to select, guide, and/or focus the heat flux from a target volume in the vicinity of the detection and reporting device.

The thermopile sensor element 170 may comprise a number of alternating pairs of thermocouples 171, 172 connected in series and separated by a thermal resistance layer or elements 173. The top thermocouple junctions 174 are at temperature T1 while the bottom thermocouple 175 junctions are at temperature T2. The output voltage V from the thermopile is usually directly proportional to the temperature difference $\Delta T=T1-T2$, across the thermal resistance layer and number of thermocouple junction pairs. The thermopile voltage output is usually also directly proportional to the heat flux q. In this way, the output voltage V between the two terminals P1 and P2 can act as an observable in the sense as explained in the embodiments of the present disclosure, so as to detect a varying incident heat, and, in turn, for example, an approaching or near hand of a user when or during using a piece of hygiene equipment.

An advantage of the described thermopile sensor element may reside in, specifically as compared to passive infrared (PIR) proximity sensors, that the output is more robust in the context of sensing the presence and action of body parts. PIR sensors may suffer from an increased dependence on whether or not the user carries gloves or the like or the body surface (skin) has varying optical properties (color, taint, hair, etc.). Since a thermopile sensor element detects and senses heat, the overall detection can be rendered more reliable in connection with detecting an instance of a user actually using a piece of hygiene equipment.

FIG. 6A shows a flow chart of a general method embodiment of the present invention. In a first step 601, an observable is sensed. This can involve any suitable type of sensor including a light sensor, an IR sensor, a UV sensor, a capacitive sensor, a force sensor, a weight sensor, a vibration sensor, an accelerometer, a switch, a threshold trigger, a Schmitt trigger, an operational amplifier, etc. A measurement result is fed to a decision step 602 that determines whether or not a use is likely. Specifically, the received measurement result can be compared to a previous result or a threshold value and/or subject to signal processing to filter out a usage over noise. If the measurement result does not indicate a likely use, then the sensing of the observable is continued with step 601.

However, when at least some likelihood for a use event can be determined in step 602, the method proceeds to step 603, in which a message is generated and transmitted. This message can contain data indicating the measurement results of the observable over some time interval, for example, in the form of a value profile. Specifically, the observable can be measured and recorded over a relevant time span (e.g., indicated by the observable value being above or below a threshold) and the resulting value-over-time-profile can be packed into the message generated in step 603. The message can also include information on determined positional information that indicates a position of the detection and reporting device. Methods and schemes for obtaining such positional information are described in conjunction with FIGS. 7A, 7B, 8A, and 8B.

In an embodiment of the present invention, a message is generated which carries information on the measured observable in a time span, such as an observable-time-profile. This data can be forwarded by means of the generated message to some kind of remote processing entity (e.g., server) for data analysis. In this way, the actual use event can be determined remotely and independent from a detection and reporting device. This also allows for more sophisticated data processing and opens the possibility to rely on more "indirect" observables, such as sound, vibration, and the like. Specifically, such observables may be subject to substantial noise or background (e.g., sound also non-related to use of hygiene equipment is present in almost all real-life scenarios), but can in this way still serve as a basis for determining a usage event.

FIG. 6B shows a flow chart of a general method embodiment of the present invention. In a step 611, an observable is measured. Similarly, as described in conjunction with FIG. 6A, a likely use may be determined before the method proceeds or, if no use is likely, the measurement of the observable is continued. However, the method may also directly proceed to step 612 in which the sensor data is processed. In this step, measurement results of the observable during a time span may be compared to one another or a single result may be compared to some predetermined or pre-stored threshold value. Further, also patterns in the form of an observable-over-time-profile may be processed for eventually determining a usage event in step 613. In a next step 614, a message is generated and transmitted that may indicate both the determination of the usage event and a position of the detection and reporting device. At this point, it should be noted that it may be sufficient to generate a message that indicates an identification and/or a position of the detection and reporting device. The fact that the message is generated and transmitted may be enough for any receiving entity to take note of the usage event.

FIGS. 7A and 7B show schematic views of locating and positioning schemes applicable for at least some embodiments of the present invention. FIG. 7A shows a schematic view of positioning equipment for determining information on a direction or an angle of arrival according to an embodiment of the present invention. Specifically, it is shown a possible implementation of a corresponding positioning device 3 which provides in this embodiment an antenna array 111 and a phase run time line 112. In this embodiment, a detection and reporting device 1 is assumed to emit a electromagnetic signal that then can reach the positioning device 3, and, with this, the antenna array 111 along two paths A and B along the line of sight. These paths will intersect a given base line with corresponding angles αA and αB. It is known to determine information on a distance and/or a position with two, three or more angles available. This concept is known as triangulation and methods exist in the arts.

The angles αA and αB can be, for example, determined by means of said phase run time line 112 where signals received by the individual antennas run and establish a certain phase relation to each other. This phase relation is a figure for a timing difference with regard to points in time when the electromagnetic signal has hit the antennas along the different paths. With this information, angles can be obtained, which can serve as a basis for determining the information on a position and/or distance. Likewise, a series of arrival times over the antenna array can be measured from which then one or more angles, and, in turn, information on a position of the originator of the electromagnetic signal can be calculated. In some embodiments, several antennas or antenna arrays may be employed for increasing precision of the obtained position information. Further, filters, such as Kalman and/or Particle filters, may be employed to increase precision, spatial resolution and/or reliability.

FIG. 7B shows a schematic view of positioning equipment for determining information on a direction or an angle of arrival according to another embodiment of the present invention. This alternative embodiment considers the device 3 being arranged to measure information on an angle αA' in the x-y-plane and an angle αA" in the x-z- or y-z-plane. Specifically, this embodiment considers an array of antennas 111 in the form of a two-dimensional matrix (as shown) or a circular matrix with antennae arranged along polar coordinates as shown in the option box O. An incoming electromagnetic signal will trigger the individual antennae of the matrix at different times and thus allows the calculation of the two angles αA' and αA" for, ultimately, determining information on a position in 2 or 3 dimensions of an electromagnetic signal source (i.e., a tag). Further, a spherical antenna may be employed that provides the individual antennae on a surface of a sphere.

FIGS. 8A and 8B show schematic views of ranging and positioning schemes applicable for at least some embodiments of the present invention. FIG. 8A shows a schematic view of a mechanism for ranging by employing a time-of-flight determination of electromagnetic signals according to an embodiment of the present invention. Specifically, FIG. 8A shows a schematic view of a general variant of so-called two way ranging (TWR) between a positioning device 3 and a detection and reporting device 1, when, for example, the device 3 acts as a beacon. It is thus assumed that the device 3 transmits beacon signals S1-1, S1-2, in regular or irregular intervals. At some given time, the device 1 can receive the beacon signal S1-3. The device 1 can obtain information on the timing when the signal S1-3 was emitted (T1) and received (T2) and obtain information on when a response signal S2 is transmitted (T3) toward and received (T4) at the device 3. Optionally, a third signal S3 can be employed to convey all the required information and data to device 1.

A payload in the beacon signal S1 may contain information on identifying the device 3, and this information may be encoded, together with relative or absolute information on the receiving/transmission timings, onto the payload of the response signal S2. The device 1 can thus obtain information on the timing when the signal S2 was received (T4) and obtain information on the timing when the signal S1-3 was transmitted (T1). Together with the timing information contained in payload data of signal S2, the device 1 is able to determine the distance d between the device 3 and the device 1 by employing a calculation such as:

$$d = c \cdot \frac{[(T4 - T1) - (T3 - T2)]}{2}, \quad (1)$$

where c denotes the speed of light, the applicable propagation speed for electromagnetic signals. Further, the conveyed payload may also be employed to ensure that the signal S2 is in actual response to the beacon signal S1-3. In addition to this, further signals may be employed for any one of improving accuracy, employing cancelling techniques or adding redundancy. If one or more additional distance(s) to another or other device(s), or one or more additional distance to device 3 (e.g., with respect to a second and further antenna thereof) is obtained, multiple distances are available for also compiling information on a relative position in two or even three dimensions.

Generally, the described electromagnetic signals can include any one of radio signals, light signals, infrared light signals, ultraviolet light signals, ultra-wide band (UWB) signals, Bluetooth™ signals, Bluetooth™ low energy (BLE) signals, and related or similar radio signals.

A similar ranging scheme can be employed where it is assumed that the device 1 transmits beacon signals S1-1, S1-2, in regular or irregular intervals. The ranging is carried out similar to the situation of FIG. 8A, taking into account— at least indirectly—the timings T1 to T4. An additional signal may be employed if the distance determination is made at the site of the device 3 but information on the determined distance should be conveyed back to the device 1.

FIG. 8B shows a schematic view of time difference of arrival (TDOA) scheme between more than one device and a detection and reporting device 1. Specifically, two devices 3 and 3' represent beacon devices and transmit beacon signals S11-1, . . . and, respectively, S12-1, . . . into some overlapping range. At some point in time, the device 1 is assumed to have received the two beacon signals S11-2 and S12-1. Both devices 3 and 3' obtain information on timing when the signals S11-1 and S12-1 are transmitted by their respectively coupled antennae. In this embodiment, the information on the timing can be identified as an instruction or synchronization signal employed for the plurality of devices 3 and 3' to transmit the signals S11-1 and S12-1 at substantially the same time T1.

In this way, the device 1 may determine different timings when the different signals are received. Namely, the signal S11-2 can be assumed to be received at T2 at device 1, and the signal S12-1 can be assumed to be received at T3 at device 1. With this knowledge, the device 1 can initiate ranging calculations. Again, further signals may be employed for any one of improving accuracy, employing cancelling techniques or adding redundancy. In addition, any determined distance or difference may be conveyed via an optional signal S21 to any one of the involved devices.

Similarly, to the one described in conjunction with FIG. 8B, the device 1 can be the originator of the beacon signal. Therefore, also the device 1 can be assumed to transmit the beacon signals at regular or irregular intervals. It may now be assumed that device 3 receives a particular signal at time T2, whereas device 3' receives this particular signal at time T3. Again, the payload carried by the signal may be employed for facilitating identification and association of any received signals. The devices can obtain information on the receiving times T2 and T3 and can decode any payload to accomplish the mentioned association, so as to determine a time difference of arrival of one signal at different locations. This information may be fed back to the device 1. As for further possible ways of initiating the sequence, it is noted that the configurations shown in the FIGS. 7A to 8B can be modified so that a device 1 is passive and 'listening' until another device sends out a signal to initiate the process (ranging).

In any way, a further embodiment of the present invention provides a detection and reporting device, wherein the positioning section acquires information that allows determining said positional information, and wherein the reporting section is configured to further transmit a message including the acquired information. For example, the information on any angles, timings, and/or signal strengths as mentioned may be wrapped in a message that is conveyed (transmitted) to a remote entity, such as a processing entity in a cloud network. Such a processing entity can then be configured to receive the acquired information and to determine positional information from information acquired by the detection and reporting device. In other words, the position of the detection and reporting device does not need to be determined locally, i.e., at the site of the detection and reporting device, but can also be determined remotely and centrally in a (cloud) network.

FIG. 9 shows a schematic and exemplary graph for values of an observable over a time span according to another embodiment of the present invention. In general, a sensor section is configured to sense over a time span an observable O indicating a use of the piece of hygiene equipment and to generate respective usage event information on the basis of the sensed observable. In an exemplary case A, an observable may be sensed at a time t1 at a given observable value O. At another time t2, the observable O may be sensed to exceed some threshold S. The fact that the observable is above (or below) a threshold can be taken as a detected usage event. The time span would in this case at least include the points in time t1 and t2.

In a further exemplary case B, the observable is sensed continuously or—in practice—at some given intervals defining the resolution. In this way the usage event information may comprise information on a profile that reflects the value O of the observable over time. This profile may provide parts that are characteristic for a usage event, e.g., the behavior of the observable O during the time span T. In this way, a usage event can be distinguished from noise or a background signal outside the use time span T.

Generally, the described observable can be analyzed locally at the site of the respective and detecting detection and reporting device or respective data on the sensed observable can be transmitted to a remote processing entity in a (cloud) network. In the former case, the detection and reporting device may include a respective analyzing section for performing this task. According to respective further embodiments of the present invention, it is also envisaged to combine any functionalities as explained in the context of the present disclosure. Specifically, any one of the described positioning, sensor, analyzing, and reporting section(s) may be implemented as one section or may share processing and/or respective memory resources, let these be local or remote.

Although detailed embodiments have been described, these only serve to provide a better understanding of the invention defined by the independent claims and are not to be seen as limiting.

What is claimed is:
1. A detection and reporting device, comprising:
a positioning section configured to acquire information relating to a relative position of the detection and reporting device to an external positioning device that allows determining positional information indicating a position of the detection and reporting device;
a sensor section configured to sense over a time span an observable indicating a use of a piece of hygiene equipment and to generate usage event information on the basis of the sensed observable; and a reporting section configured to generate and transmit a message on the basis of said usage event information and on the acquired information allowing an association to said positional information.

2. The detection and reporting device according to claim 1, further comprising a processing section configured to process said usage event information for determining said usage event, and wherein said reporting section is configured to generate and transmit said message when a usage event is determined.

3. The detection and reporting device according to claim 2, wherein the processing section is configured to process said usage event information for obtaining additional information.

4. The detection and reporting device according to claim 3, wherein said additional information includes any one of an amount of a consumable ejected by the piece of hygiene equipment, an amount of soap ejected by the piece of hygiene equipment, an amount of a disinfectant ejected by the piece of hygiene equipment, and a type of a consumable.

5. The detection and reporting device according to claim 1, wherein the positioning section is configured to receive and/or transmit electromagnetic signals.

6. The detection and reporting device according to claim 5, wherein the positioning section is configured to obtain timing information indicating timings when electromagnetic signals are received and/or transmitted.

7. The detection and reporting device according to claim 6, wherein the positioning section is configured to process said timing information for obtaining said information indicating the position of the detection and reporting device.

8. The detection and reporting device according to claim 1, wherein the sensor section includes a sensor for sensing any one of proximity of an object, a light intensity, an IR light intensity, an UV light intensity, a vibration, a sound, a weight, a force, an electric signal, a temperature, a heat flux, a movement of an object, a time-of-flight measurement, a concentration of a gas component in air, a concentration of a vapor component in air, a concentration of a particle component in air.

9. The detection and reporting device according to claim 1, wherein the sensor section includes a thermopile.

10. The detection and reporting device according to claim 1, wherein the sensor section includes a switch arranged to be in an operable interaction to an ejection mechanism of the piece of hygiene equipment.

11. The detection and reporting device according to claim 1, further comprising a fixing section including any one of an adhesive pad, an adhesive tape, a bore, a clip, a hook, an engagement member, a screw, and a magnet.

12. The detection and reporting device according to claim 1, wherein said reporting section is configured to generate said message on the basis of any one of an information on an amount of an ejected consumable, information on a type of an ejected consumable, time information, position information, location information, and identification information.

13. The detection and reporting device according to claim 1, wherein said reporting section is configured to transmit said message after a predetermined number of usage events have been determined.

14. The detection and reporting device according to claim 1, wherein said reporting section is configured to transmit said message in predetermined intervals for none, one, or more than one determined usage event.

15. The detection and reporting device according to claim 1, further comprising a time keeping section providing time information, and wherein the reporting section is configured to generate said message further on the basis of said time information.

16. The detection and reporting device according to claim 1, further being configured to accompany a mobile piece of hygiene equipment.

17. The detection and reporting device according to claim 1, wherein the detection and reporting device determines the usage event indicating the use of the piece of hygiene equipment.

18. A system comprising a detection and reporting device according to claim 1, and a processing entity configured to receive the acquired information and to determine positional information from information acquired by the detection and reporting device.

19. A method for detecting a usage event indicating a use of a piece of hygiene equipment, comprising the steps of:

determining positional information indicating a position of the piece of hygiene equipment from information acquired by the piece of hygiene equipment relating to a relative position of the piece of hygiene equipment to an external positioning device that allows the determining of the positional information indicating the position of the piece of hygiene equipment;

sensing over a time span an observable indicating the use of the piece of hygiene equipment and generating usage event information on the basis of the sensed observable; and generating and transmitting a message on the basis of said usage event information and on the acquired information allowing the association to said positional information.

* * * * *